(12) United States Patent
Saoji et al.

(10) Patent No.: US 8,209,025 B1
(45) Date of Patent: *Jun. 26, 2012

(54) METHODS AND SYSTEMS OF OPTIMIZING STIMULATION CURRENT APPLIED TO A COCHLEAR IMPLANT PATIENT

(75) Inventors: Aniket Saoji, Newhall, CA (US); Leonid M. Litvak, Los Angeles, CA (US)

(73) Assignee: Advanced Bionics, LLC, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/217,697

(22) Filed: Aug. 25, 2011

Related U.S. Application Data (62) Division of application No. 12/059,358, filed on Mar. 31, 2008, now Pat. No. 8,027,734.

(60) Provisional application No. 60/949,715, filed on Jul. 13, 2007.

(51) Int. Cl.
*A61N 1/06* (2006.01)

(52) U.S. Cl. .............. 607/57; 607/55; 607/56

(58) Field of Classification Search .......... 607/55–57; 600/25, 372, 379, 559
See application file for complete search history.

(56) References Cited

U.S. PATENT DOCUMENTS

| | | | |
|---|---|---|---|
| 4,390,748 A * | 6/1983 | Zwicker | 73/585 |
| 4,400,590 A | 8/1983 | Michelson | |
| 4,532,930 A | 8/1985 | Crosby et al. | |
| 4,592,359 A | 6/1986 | Galbraith | |
| 4,947,844 A | 8/1990 | McDermott | |
| 5,824,022 A | 10/1998 | Zilberman et al. | |
| 6,157,861 A * | 12/2000 | Faltys et al. | 607/57 |
| 6,219,580 B1 | 4/2001 | Faltys et al. | |
| 6,272,382 B1 | 8/2001 | Faltys et al. | |
| 6,308,101 B1 | 10/2001 | Faltys et al. | |
| 8,027,734 B1 * | 9/2011 | Saoji et al. | 607/57 |

OTHER PUBLICATIONS

Eddins, David A. et al., "Spectral modulation detection as a function of modulation frequency, carrier bandwidth, and carrier frequency region", J. Acoust. Soc. Am. 121 (1) (Jan. 2007).

Drennan, Ward R. et al., "Current-Level Discrimination in the Context of Interleaved, Multichannel Stimulation in Cochlear Implants: Effects of Number of Stimulated Electrodes, Pulse Rate, and Electrode Separation", JARO 7:308-316 (Jun. 21, 2006).

* cited by examiner

*Primary Examiner* — Rex R Holmes
(74) *Attorney, Agent, or Firm* — AdvantEdge Law Group, LLC

(57) ABSTRACT

Methods of optimizing stimulation current applied to a cochlear implant patient include determining a plurality of narrowband spectral modulation detection thresholds for the patient and adjusting a stimulation current applied to the patient in accordance with the narrowband spectral modulation detection thresholds. Systems for optimizing stimulation current applied to a cochlear implant patient include an electrode array having a plurality of electrodes disposed thereon, an implantable cochlear stimulator coupled to the electrode array and configured to apply a stimulation current to one or more locations along a cochlea of a patient via one or more of the electrodes, and a fitting station communicatively coupled to the implantable cochlear stimulator. The fitting station is configured determine a plurality of narrowband spectral modulation detection thresholds and adjust the stimulation current in accordance with the narrowband spectral modulation detection thresholds.

19 Claims, 8 Drawing Sheets

METHODS AND SYSTEMS OF OPTIMIZING STIMULATION CURRENT APPLIED TO A COCHLEAR IMPLANT PATIENT

RELATED APPLICATIONS

The present application is a divisional application of U.S. patent application Ser. No. 12/059,358, filed Mar. 31, 2008, which application issued as U.S. Pat. No. 8,027,734 on Sep. 27, 2011 and claims priority under 35 U.S.C. §119(e) to U.S. Provisional Patent Application No. 60/949,715, filed Jul. 13, 2007. Both applications are incorporated herein by reference in their respective entireties.

BACKGROUND INFORMATION

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that acoustic signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce acoustic signals into auditory nerve impulses. Thus, people who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems generally employ an electrode array that is inserted into the cochlear duct. One or more electrodes of the array selectively stimulate different auditory nerves at different places in the cochlea based on the pitch of a received sound signal. Within the cochlea, there are two main cues that convey "pitch" (frequency) information to the patient. These are (1) the place or location of stimulation along the length of a cochlear duct and (2) the temporal structure of the stimulating waveform. In the cochlea, sound frequencies are mapped to a "place" in the cochlea, generally from low to high sound frequencies mapped from the apical to basilar direction. The electrode array is fitted to the patient to arrive at a mapping scheme such that electrodes near the base of the cochlea are stimulated with high frequency signals, while electrodes near the apex are stimulated with low frequency signals.

A sound processing strategy is an algorithm that translates signals detected by a microphone into a sequence of electric pulses that can be transmitted to the intra-cochlear electrodes. However, cochlear implant patients vary greatly in their capability to comprehend speech and other sounds in difficult listening situations. Some of the variability can be attributed to differences in the ability of the patients to process complex stimulation patterns generated across an electrode array. Furthermore, the ability to process complex patterns may differ from patient to patient across different regions of the electrode array. Hence, it is currently difficult to determine optimum sound processing strategies for different patients.

SUMMARY

Methods of optimizing stimulation current applied to a cochlear implant patient include determining a plurality of narrowband spectral modulation detection thresholds for the patient and adjusting a stimulation current applied to the patient in accordance with the narrowband spectral modulation detection thresholds.

Systems for optimizing stimulation current applied to a cochlear implant patient include an electrode array having a plurality of electrodes disposed thereon, an implantable cochlear stimulator coupled to the electrode array and configured to apply a stimulation current to one or more locations along a cochlea of a patient via one or more of the electrodes, and a fitting station communicatively coupled to the implantable cochlear stimulator. The fitting station is configured determine a plurality of narrowband spectral modulation detection thresholds and adjust the stimulation current in accordance with the narrowband spectral modulation detection thresholds.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Methods and systems of optimizing stimulation current that is applied to a cochlear implant patient are described herein. A plurality of narrowband spectral modulation detection thresholds for the patient are determined by measuring the spectral modulation detection thresholds (SMDTs) for a plurality of narrowband frequency ranges. The stimulation current applied to the patient may then be adjusted in accordance with the measured narrowband spectral modulation detection thresholds.

In the following description, for purposes of explanation, numerous specific details are set forth in order to provide a thorough understanding of the present systems and methods.

It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

To facilitate an understanding of the methods and systems described herein, an exemplary cochlear implant system 100 will now be described in connection with FIG. 1. Exemplary cochlear implant systems suitable for use as described herein include, but are not limited to, those disclosed in U.S. Pat. Nos. 4,400,590; 4,532,930; 4,592,359; 4,947,844; 5,824,022; 6,219,580; 6,272,382; and 6,308,101. All of these listed patents are incorporated herein by reference in their respective entireties.

Figure 1:
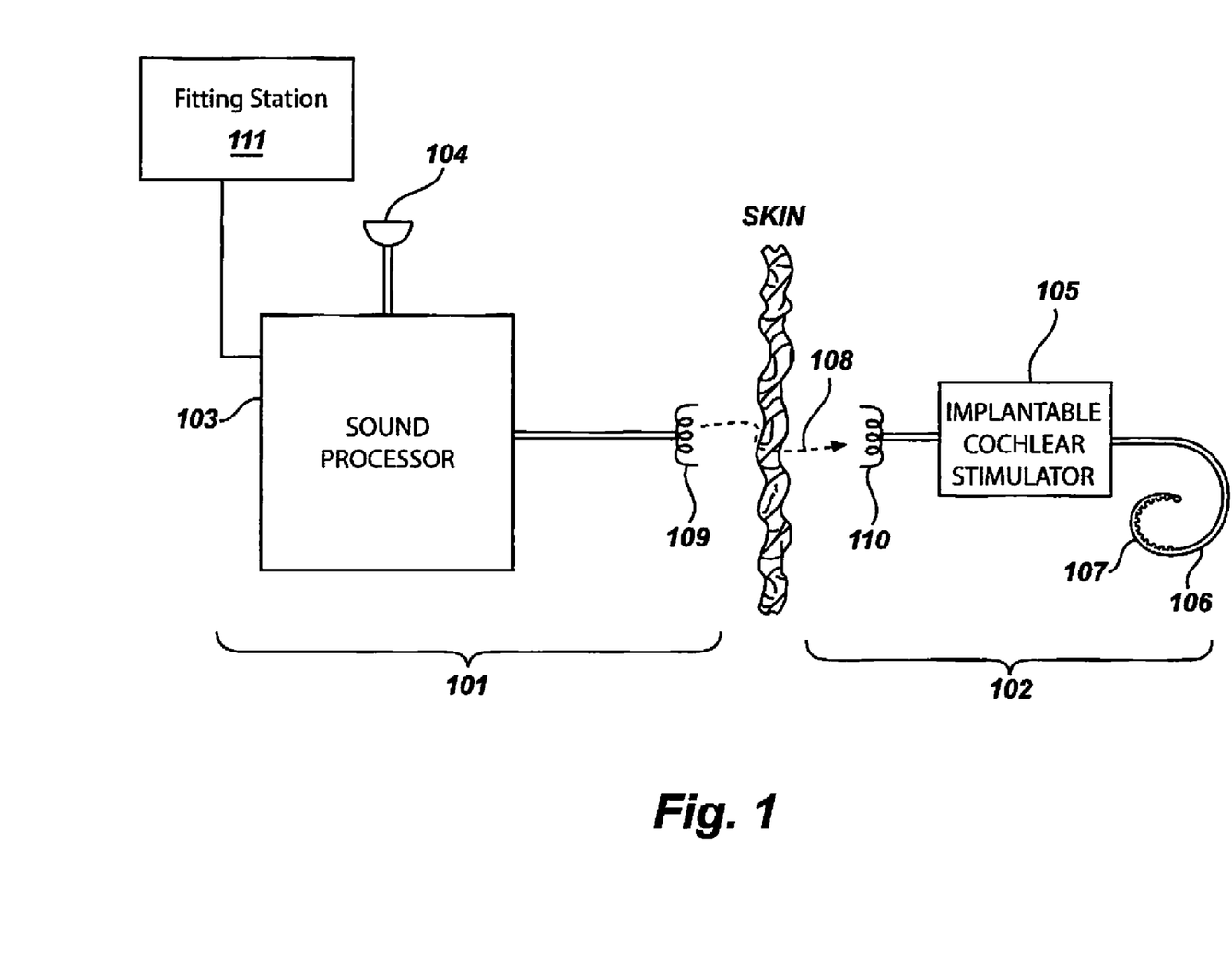
FIG. 1 illustrates an exemplary cochlear implant system according to principles described herein.

As shown in FIG. 1, the cochlear implant system 100 includes an external sound processor portion 101 and an implanted cochlear stimulation portion 102. The sound processor portion 101 may include a sound processing unit 103, a microphone 104, and/or additional circuitry as best serves a particular application. The cochlear stimulation portion 102 may include an implantable cochlear stimulator (ICS) 105, a lead 106 with an array of electrodes 107 disposed thereon, and/or additional circuitry as best serves a particular application. It will be recognized that the sound processor portion 101 may alternatively be located internal to the patient.

The microphone 104 of FIG. 1 is configured to sense acoustic signals and convert the sensed signals to corresponding electrical signals. The electrical signals are sent to the sound processing unit 103 over an electrical or other suitable link. Alternatively, the microphone 104 may be connected directly to, or integrated with, the sound processing unit 103.

The sound processing unit 103 may include any combination of hardware, software, and/or firmware as best serves a particular application. For example, the sound processing unit 103 may include one or more processors, digital signal processors (DSPs), filters, memory units, etc.

In some examples, the sound processing unit 103 may be configured to process the converted acoustic signals in accordance with a selected sound processing strategy to generate appropriate control signals or stimulation parameters for controlling the ICS 105. It will be recognized that the sound processing unit 103 shown in FIG. 1 is merely illustrative of the many different sound processing units that may be used in connection with the present systems and methods. For example, the sound processing unit 103 may include a behind-the-ear (BTE) unit configured to be positioned behind the ear. Alternatively, the sound processing unit 103 may include a portable speech processor (PSP) device, a conventional hearing aid, or any other type of signal processing unit.

The lead 106 of FIG. 1 is adapted to be inserted within a duct of a patient's cochlea. As shown in FIG. 1, the lead 106 includes an array of electrodes 107 disposed along its length. It will be recognized that any number of electrodes 107 may be disposed along the lead 106 as may serve a particular application.

Each of the electrodes 107 is electrically coupled to the ICS 105. Electronic circuitry within the ICS 105 may therefore be configured to apply stimulation current to selected pairs or groups of electrodes 107 in accordance with a specified stimulation pattern controlled by the sound processing unit 103.

As mentioned, the ICS 105 and lead 106 may be implanted within the patient while the sound processing unit 103 and the microphone 104 are configured to be located outside the patient, e.g., behind the ear. Hence, the ICS 105 and the sound processing unit 103 may be transcutaneously coupled via a suitable data or communications link 108. The communications link 108 allows power and control signals to be sent from the sound processing unit 103 to the ICS 105. In some embodiments, data and status signals may also be sent from the ICS 105 to the sound processing unit 103.

The external and implantable portions of the cochlear implant system 100 may each include one or more coils configured to transmit and receive power and/or control signals via the data link 108. For example, the external portion 101 of the cochlear implant system 100 may include an external coil 109 and the implantable portion of the cochlear implant system 102 may include an implantable coil 110. The external coil 109 and the implantable coil 110 may be inductively coupled to each other, thereby allowing data and power signals to be wirelessly transmitted between the external portion and the implantable portion of the cochlear implant system 100.

When a cochlear implant system is initially implanted in a patient, and during follow-up tests and checkups thereafter, it is usually necessary to fit the cochlear implant system to the patient. Such "fitting" includes adjustment of the sound processing strategy and/or stimulation parameters such that the various stimuli generated by the cochlear implant system are most effective for the patient. To this end, as shown in FIG. 1, a fitting station 111 may be communicatively coupled to the sound processing unit 103. The fitting station 111 may include any suitable external device such as a personal computer, handheld device, programming device, or the like, and may be used by a clinician to fit the cochlear implant system 100 to a particular patient.

However, as mentioned previously, cochlear implant patients vary greatly in their ability to comprehend speech and other sounds in difficult listening situations. For example, it is difficult for some cochlear implant patients to recognize speech in the presence of background noise. Some of the difficulty can be attributed to differences in the patients' ability to process complex stimulation patterns generated across the electrode array.

It is believed that the ability of a patient to process complex stimulation patterns may further vary across different regions of an electrode array (i.e., across different narrowband frequency ranges). For example, there may be a dead region within the cochlea of a particular patient. In this case, the patient may be unable to process complex stimulation patterns applied by the electrode array to the dead region of the cochlea. However, the patient may still be able to process complex stimulation patterns applied to other regions of the cochlea that are functioning properly.

Hence, the methods and systems described herein may be used to determine the ability of a patient to distinguish electrically generated complex stimulation patterns within one or more narrowband frequency ranges. As will be described in more detail below, once the ability of the patient to distinguish electrically generated complex stimulation patterns within a particular narrowband frequency range is determined, the stimulation parameters may be adjusted to optimize the stimulation that is applied to the patient within that frequency range.

In some examples, the ability of a patient to distinguish electrically generated complex stimulation patterns within one or more narrowband frequency ranges that correspond to one or more portions of an electrode array may be measured by determining one or more spectral modulation detection thresholds (SMDTs) for that patient. As used herein, the term "spectral modulation detection threshold" refers to the minimum spectral contrast needed for a patient to distinguish between a stimulus having an unmodulated or flat pattern across a specified frequency range and a spectrally modulated stimulus having a ripple pattern across the specified frequency range. The term "spectral contrast" will be described below in connection with FIGS. 2A-2B.

Figure 2A:
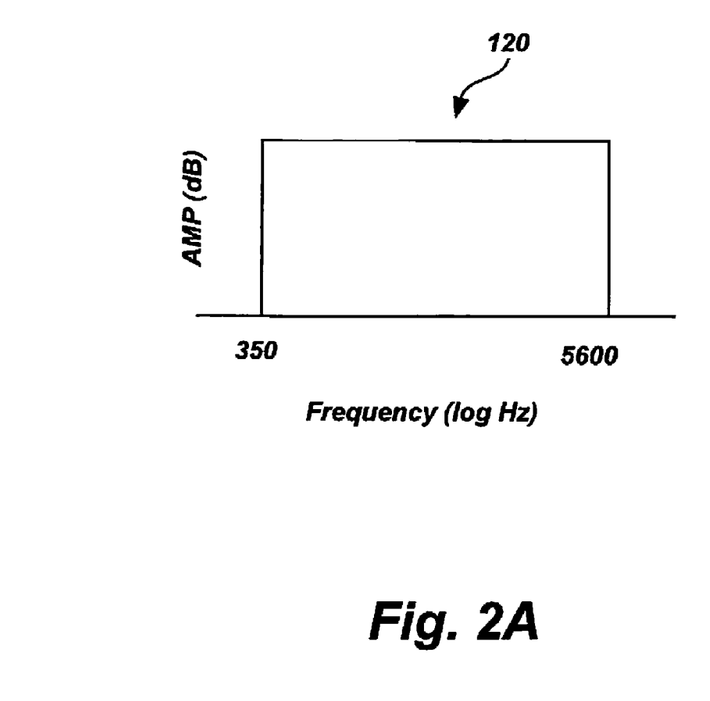
FIGS. 2A-2B illustrate the difference between a stimulus having a flat pattern across a specified frequency range and a spectrally modulated stimulus having a ripple pattern across the frequency range according to principles described herein.
Figure 2B:
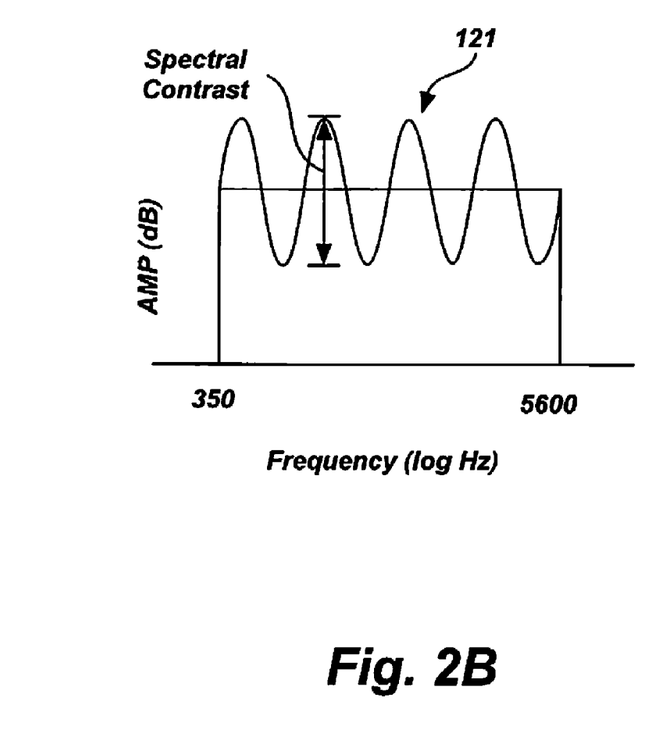

FIGS. 2A-2B illustrate the difference between a stimulus 120 having a flat pattern across a specified frequency range (FIG. 2A) and a spectrally modulated stimulus 121 having a ripple pattern across the frequency range (FIG. 2B). The horizontal axes in FIGS. 2A-2B represent frequency and the vertical axes represent the amplitude in decibels (dB) of the stimuli. The frequency range shown in FIGS. 2A and 2B is merely illustrative and may include any range of frequencies as may serve a particular application.

As shown in FIG. 2A, the flat stimulus 120 has a constant amplitude across the entire frequency range of interest. However, the spectrally modulated stimulus 121 includes a modulating waveform (e.g., a sinusoid) within the frequency range of interest. As shown in FIG. 2B, the peak-to-valley amplitude of the modulating waveform is referred to as the spectral contrast. As will be described in more detail below, the spectral contrast of a spectrally modulated stimulus 121 may be varied as may best serve a particular application.

Figure 3:
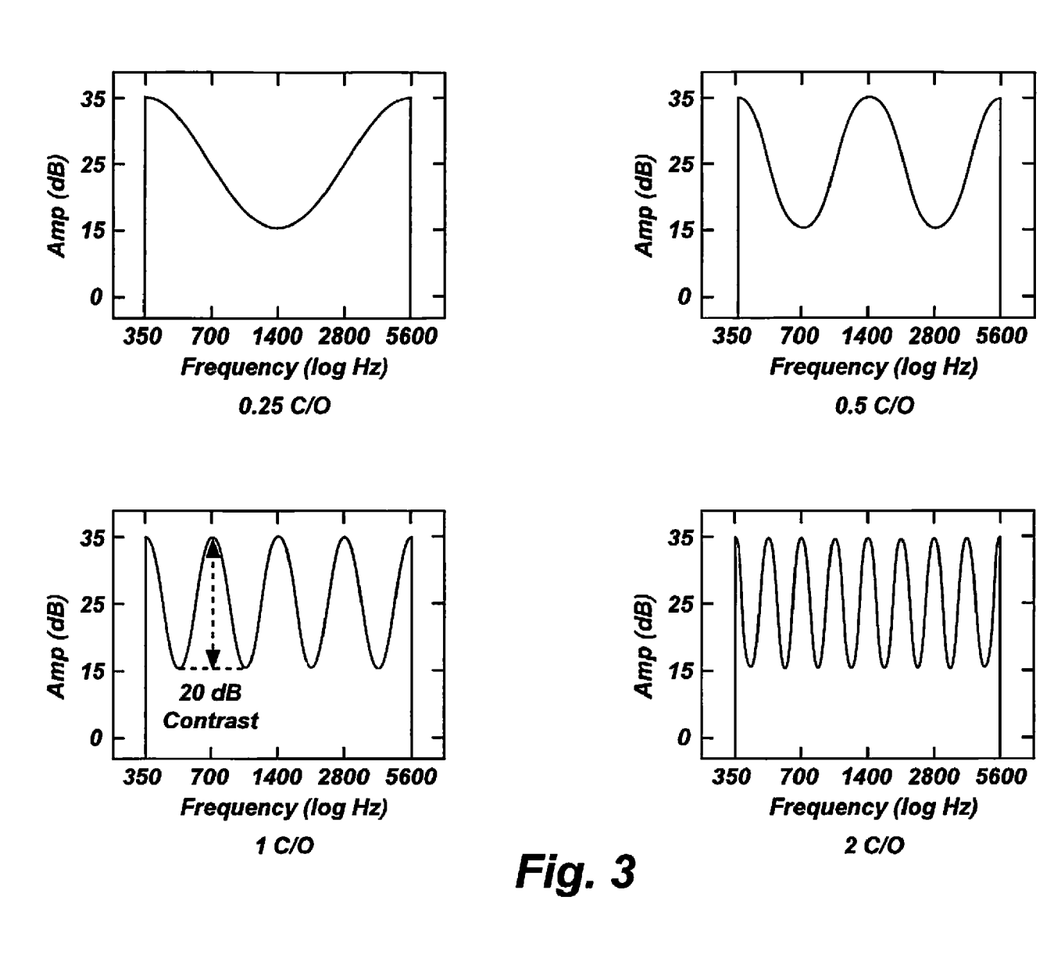
FIG. 3 illustrates a number of spectrally modulated stimuli according to principles described herein.

It will be recognized that the spectrally modulated stimulus 121 illustrated in FIG. 2B is merely illustrative of the many different spectrally modulated stimuli that may be used in connection with the methods and systems described herein. For example, FIG. 3 illustrates a number of spectrally modulated stimuli that may be used in connection with the methods and systems described herein. As illustrated in FIG. 3, each spectrally modulated stimulus may include ripple patterns with different ripple frequencies (measured in cycles per octave (c/o)) and with different amplitudes.

Figure 4:
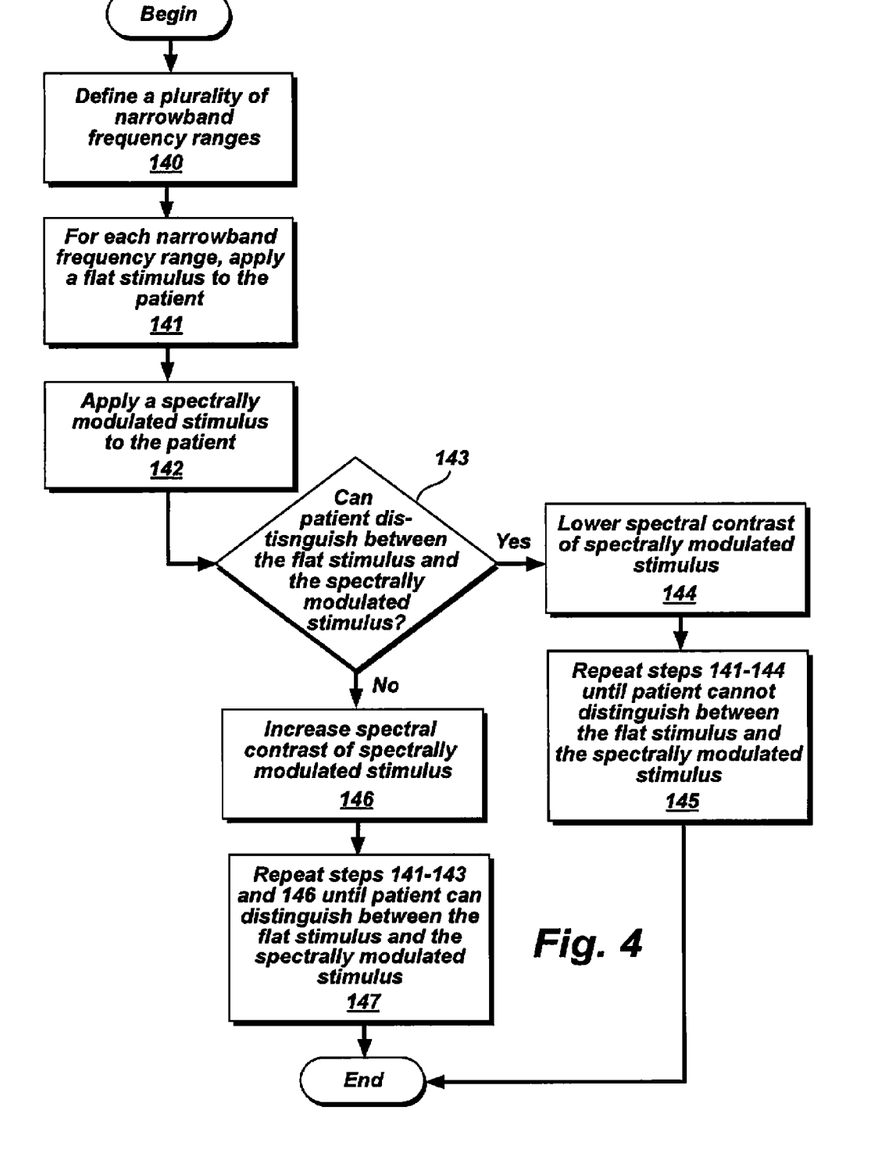
FIG. 4 is a flow chart illustrating an exemplary method of measuring spectral modulation detection thresholds across various narrowband frequency regions for a particular patient according to principles described herein.

FIG. 4 is a flow chart illustrating an exemplary method of measuring spectral modulation detection thresholds across various narrowband frequency regions for a particular patient. The steps illustrated in FIG. 4 may be modified, reordered, and/or added to as may serve a particular application.

In step 140, a plurality of narrowband frequency ranges are defined. For example, three narrowband frequency ranges may be defined: 350 to 1400 Hz, 700 to 2800 Hz, and 1400 to 5600 Hz. It will be recognized that the frequency ranges may or may not overlap as may serve a particular application. Moreover, it will be recognized that the frequencies included in each range and the total number of narrowband frequency ranges that are defined may vary as may serve a particular application.

Once the narrowband frequency ranges have been defined, the spectral modulation detection thresholds for each frequency range may be determined. To this end, a flat stimulus and a spectrally modulated stimulus may be applied to the cochlea via the portion of the electrode array that corresponds to the particular narrowband frequency range of interest, as shown in steps 141 and 142.

Figure 5:
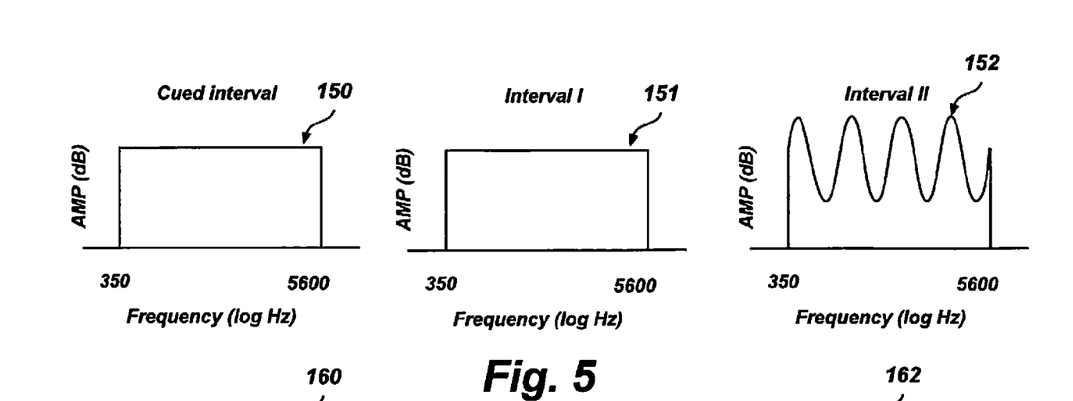
FIG. 5 illustrates an exemplary cued, two-interval, two-alternative, forced-choice paradigm that may be used according to principles described herein.

In some examples, the flat and spectrally modulated stimuli are applied according to a cued, two-interval, two-alternative, forced-choice paradigm. FIG. 5 illustrates an exemplary cued, two-interval, two-alternative, forced-choice paradigm that may be used in accordance with the methods and systems described herein. As shown in FIG. 5, a cued stimulus 150 may be applied first during a cued interval, followed by a flat stimulus 151 during a first interval and then by a spectrally modulated stimulus 152 during a second interval. It will be recognized that the order in which the flat and spectrally modulated stimuli are applied may vary as may serve a particular application.

As shown in FIG. 5, the cued stimulus 150 and the flat stimulus 151 may be substantially similar in some examples. However, it will be recognized that the cued stimulus 150 and the flat stimulus 151 may differ in other examples.

Figure 6A:
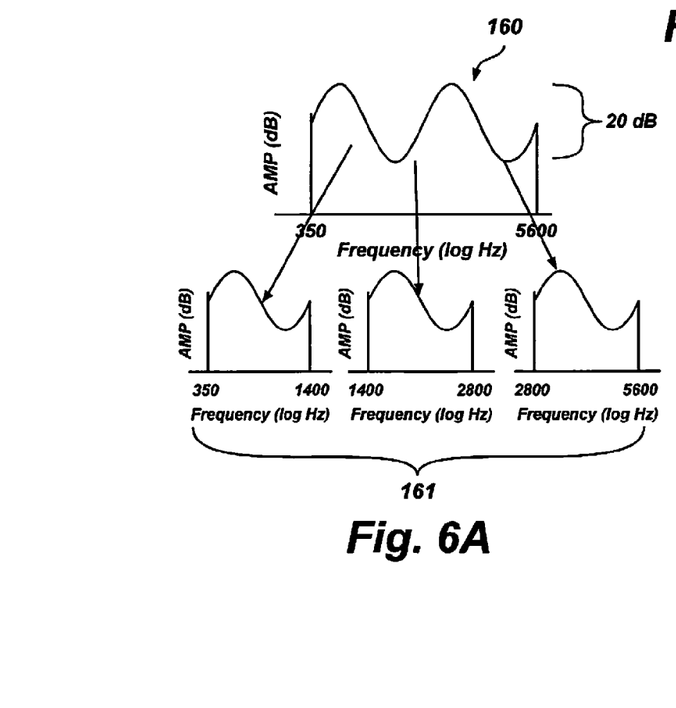
FIGS. 6A-6B are schematic representations of spectrally modulated stimuli with modulation frequencies of 0.5 cycles/octave and 1.0 cycles/octave with broadband carriers and narrowband carriers according to principles described herein.
Figure 6B:
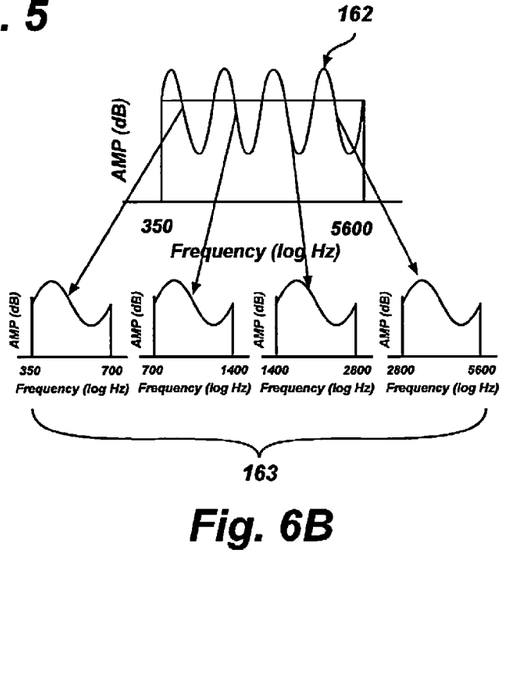

As mentioned, the particular stimulation parameters corresponding to the spectrally modulated stimulus that is applied may vary as may serve a particular application. For example, the spectrally modulated stimulus may have a modulation frequency of 0.5 cycles/octave (c/o), 1.0 cycles/octave, or any other value as may serve a particular application. To illustrate, FIG. 6A is a schematic representation of spectrally modulated stimuli with modulation frequencies of 0.5 cycles/octave. Stimulus 160 includes a broadband carrier and stimuli 161 include narrowband carriers. FIG. 6B is a schematic representation of spectrally modulated stimuli with modulation frequencies of 1.0 cycles/octave. Stimulus 162 includes a broadband carrier and stimuli 163 include narrowband carriers.

Other stimulation parameters of the spectrally modulated stimuli that are applied to the cochlea may also be varied. For example, the spectral phase may be randomized across trials to restrict local increment detection. The presentation level may be 60 dB SPL or any other value as may serve a particular application.

Returning to FIG. 4, once the flat and spectrally modulated stimuli are applied within a particular narrowband frequency range, it is determined whether the patient is able to distinguish between the two stimuli, as shown in step 143. The particular manner in which it is determined whether the patient is able to distinguish between the flat and spectrally modulated stimuli may vary as may serve a particular application. For example, the clinician may rely on patient feedback, sensed indicators, or any other factor in determining whether the patient is able to distinguish between the flat and spectrally modulated stimuli.

If it is determined that the patient is able to distinguish between the two stimuli, the spectral contrast of the spectrally modulated stimulus is lowered (step 144) and steps 141-144 are repeated until the patient cannot distinguish between the flat stimulus and the spectrally modulated stimulus (step 145). The point at which the patient first cannot distinguish between the flat and spectrally modulated stimuli corresponds to the spectral modulation detection threshold for that particular narrowband frequency range.

However, if it is determined that the patient cannot distinguish between the two stimuli, the spectral contrast of the spectrally modulated stimulus is increased (step 146) and steps 141-143 and 146 are repeated until the patient can distinguish between the flat stimulus and the spectrally modulated stimulus (step 147). The point at which the patient can first distinguish between the flat and spectrally modulated stimuli corresponds to the spectral modulation detection threshold for that particular narrowband frequency range.

The method described in connection with FIG. 4 may be repeated for all of the narrowband frequency ranges to determine the spectral modulation detection thresholds for each of the narrowband frequency ranges. In some examples, the method described in connection with FIG. 4 may be repeated multiple times for a particular narrowband frequency range and the results averaged to determine the spectral modulation detection threshold for that particular narrowband frequency range.

Figure 7:
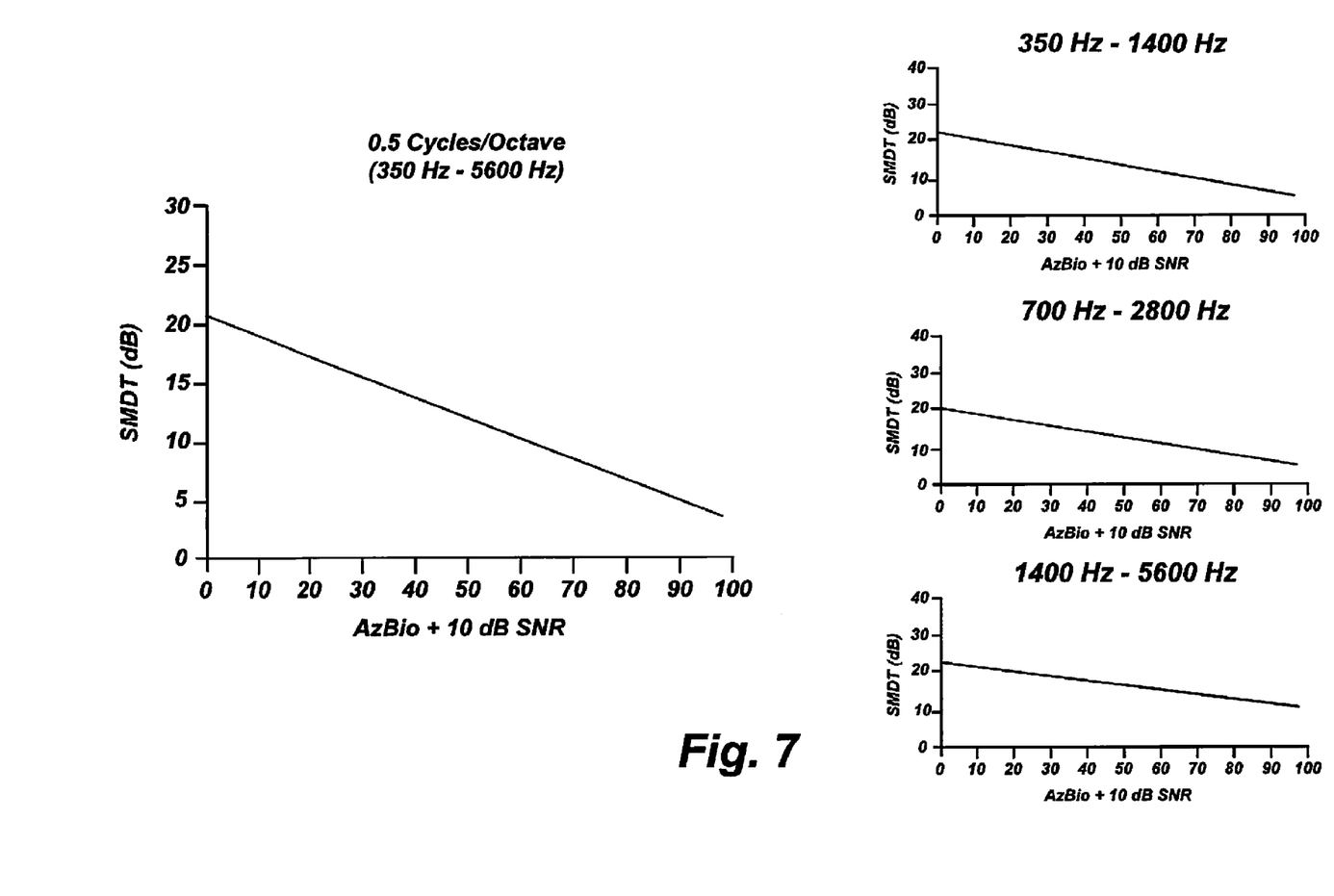
FIGS. 7-8 show the correlation between speech understanding scores and spectral modulation detection thresholds obtained within various narrowband frequency ranges according to principles described herein.
Figure 8:
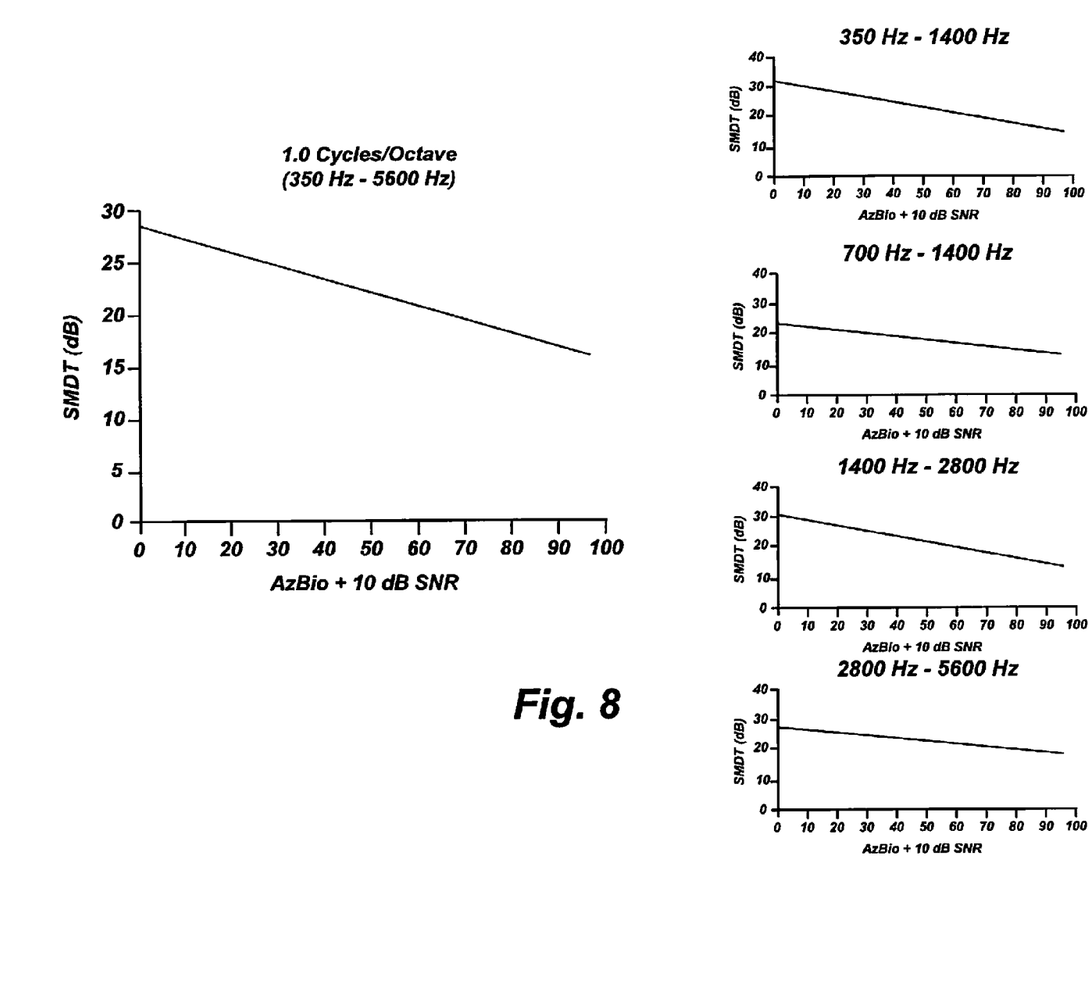

FIGS. 7-8 show a correlation between speech understanding scores and spectral modulation detection thresholds obtained within various broadband and narrowband frequency ranges. FIG. 7 corresponds to a modulation frequency of 0.5 cycles/octave and FIG. 8 corresponds to a modulation frequency of 1.0 cycles/octave. As shown in the graphs of FIGS. 7-8, speech understanding scores (represented by the x-axis) increase as the spectral modulation detection thresholds decrease for both the broadband and narrowband frequency ranges.

Figure 9:
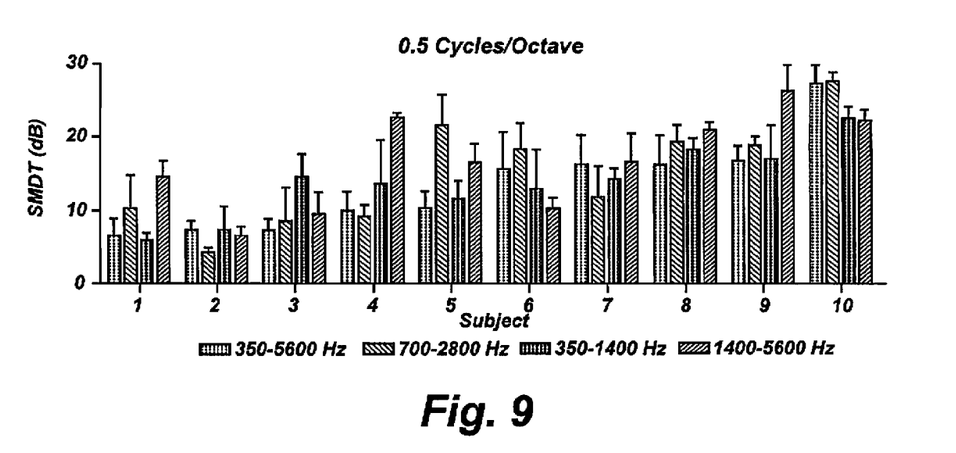
FIGS. 9-10 illustrate the effect of the narrowband spectral modulation detection thresholds on the spectral modulation detection threshold across the entire broadband frequency spectrum according to principles described herein.
Figure 10:
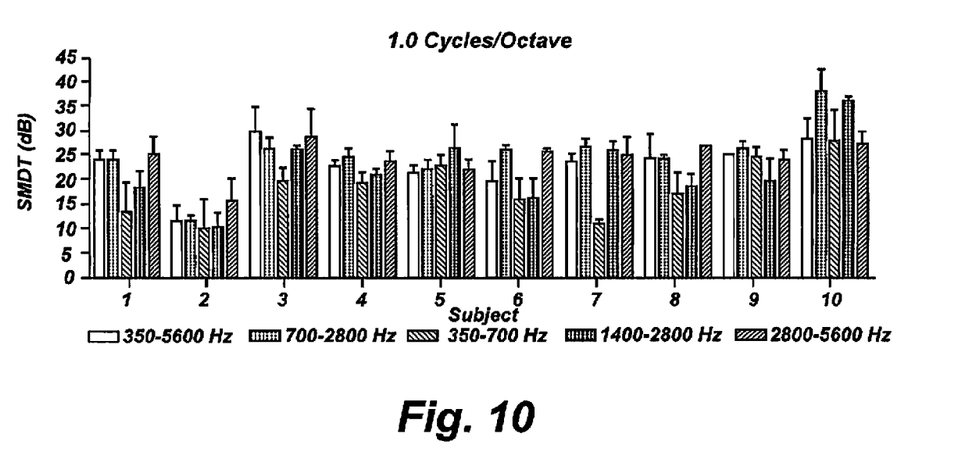

FIGS. 9-10 illustrate the effect of the narrowband spectral modulation detection thresholds on the spectral modulation detection threshold across the entire broadband frequency spectrum (e.g., between 350 and 5600 Hz) for ten patients or subjects. FIG. 9 corresponds to a modulation frequency of 0.5 cycles/octave and FIG. 10 corresponds to a modulation frequency of 1.0 cycles/octave. The first vertical bar for each subject represents the broadband spectral modulation detection threshold and the remaining vertical bars for each subject represent the various narrowband spectral modulation detection thresholds. Hence, by determining the spectral modulation detection thresholds for a plurality of narrowband frequency ranges, a clinician may determine which portions of the cochlea are responsible for overall sub-optimal cochlear implant performance by noting which narrowband spectral modulation detection threshold(s) are abnormally high.

Once the narrowband spectral modulation detection thresholds have been determined, various adjustments to the stimulation applied via the electrode array may be made to improve overall performance of the cochlear implant system. For example, if a patient exhibits an abnormally high spectral modulation detection threshold within a particular narrowband frequency range, one or more of the stimulation parameters (e.g., electrode configuration, pulse width, pulse shape, amplitude, frequency, IDR, etc.) that control the stimulation applied via the corresponding group of electrodes within the electrode array may be adjusted to optimize the ability of the patient to detect and understand sound within that frequency range.

Additionally or alternatively, the spectral features of the affected narrowband frequency range may be discriminated in order to compensate for the abnormally high spectral modulation detection threshold. In other words, the deficiency within the affected narrowband frequency range may be exaggerated to compensate for the abnormally high spectral modulation detection threshold.

Additionally or alternatively, the stimulation to be applied within an affected narrowband frequency range may be reallocated to be applied via electrodes assigned to other frequency ranges. For example, if a patient exhibits an abnormally high spectral modulation detection threshold within a first narrowband frequency range (e.g., 700-1400 Hz), the stimulation that would typically be applied via electrodes assigned to that frequency range may be reallocated and applied via electrodes assigned to a second narrowband frequency range (e.g., 1400-2800 Hz). It will be recognized that the frequency reallocation among the different electrodes may be performed according to any suitable method.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
   an electrode array having a plurality of electrodes disposed thereon;
   an implantable cochlear stimulator coupled to the electrode array and configured to apply a stimulation current to one or more locations along a cochlea of a patient via one or more of the electrodes; and
   a fitting station communicatively coupled to the implantable cochlear stimulator;
   wherein the fitting station is configured determine a plurality of narrowband spectral modulation detection thresholds and adjust the stimulation current in accordance with the narrowband spectral modulation detection thresholds; and
   wherein the fitting station is configured to determine the narrowband spectral modulation detection thresholds by
      defining a plurality of narrowband frequency ranges,
      applying a flat electrical stimulus within each of the frequency ranges to the patient,
      applying a spectrally modulated electrical stimulus within each of the frequency ranges to the patient, and
      modulating a spectral contrast of the spectrally modulated electrical stimuli to a smallest value at which the patient is able to distinguish between the flat electrical stimuli and the spectrally modulated electrical stimuli.

2. The system of claim 1, wherein each of the spectrally modulated electrical stimuli has a modulation frequency substantially equal to 0.5 cycles per octave.

3. The system of claim 1, wherein each of the spectrally modulated electrical stimuli has a modulation frequency substantially equal to 1.0 cycles per octave.

4. The system of claim 1, further comprising reallocating at least a portion of the stimulation current from one of the narrowband frequency ranges to another of the narrowband frequency ranges in accordance with at least one of the narrowband spectral modulation detection thresholds.

5. A system comprising:
   an implantable cochlear stimulator configured to be implanted within a patient; and
   a fitting station communicatively coupled to the implantable cochlear stimulator and configured to determine a plurality of narrowband spectral modulation detection thresholds for the patient by
      defining a plurality of narrowband frequency ranges each associated with one of the narrowband spectral modulation detection thresholds,
      directing the implantable cochlear stimulator to apply a flat electrical stimulus within each of the narrowband frequency ranges to the patient,
      directing the implantable cochlear stimulator to apply a spectrally modulated electrical stimulus within each of the narrowband frequency ranges to the patient, and
      modulating a spectral contrast of the spectrally modulated electrical stimulus within each of the narrowband frequency ranges to a smallest value at which the patient is able to distinguish between the flat electrical stimulus and the spectrally modulated electrical stimulus;
   wherein the fitting station is further configured to direct the implantable cochlear stimulator to adjust a stimulation current applied to the patient in accordance with the narrowband spectral modulation detection thresholds.

6. The system of claim 5, wherein the spectrally modulated electrical stimulus has a modulation frequency substantially equal to 0.5 cycles per octave.

7. The system of claim 5, wherein the spectrally modulated electrical stimulus has a modulation frequency substantially equal to 1.0 cycles per octave.

8. The system of claim 5, wherein the fitting station is configured to direct the implantable cochlear stimulator to adjust the stimulation current by adjusting one or more stimulation parameters that control the stimulation current.

9. The system of claim 5, wherein the fitting station is further configured to reallocate the stimulation current between one or more narrowband frequency ranges in accordance with the narrowband spectral modulation detection thresholds.

10. The system of claim 5, wherein the spectrally modulated electrical stimulus has a ripple pattern.

11. The system of claim 5, further comprising:
an electrode array coupled to the implantable cochlear stimulator and having a plurality of electrodes disposed thereon;
wherein the implantable cochlear stimulator is configured to apply the flat electrical stimulus and the spectrally modulated electrical stimulus to one or more locations along a cochlea of the patient via one or more of the electrodes.

12. A system comprising:
an implantable cochlear stimulator configured to be implanted within a patient; and
a fitting station communicatively coupled to the implantable cochlear stimulator and configured to
determine a plurality of narrowband spectral modulation detection thresholds for the patient by defining a plurality of narrowband frequency ranges each associated with one of the narrowband spectral modulation detection thresholds, and
adjust a stimulation current applied by the implantable cochlear stimulator to the patient in accordance with the narrowband spectral modulation detection thresholds;
wherein, for a particular narrowband frequency range included in the plurality of the narrowband frequency ranges, the fitting station is configured to determine a narrowband spectral modulation threshold that corresponds to the particular narrowband frequency range by directing the implantable cochlear stimulator to apply a flat electrical stimulus and a spectrally modulated electrical stimulus within the particular narrowband frequency range to the patient in accordance with a cued, two-interval, two-alternative, forced-choice paradigm, and
modulating a spectral contrast of the spectrally modulated electrical stimulus to a smallest value at which the patient is able to distinguish between the flat electrical stimulus and the spectrally modulated electrical stimulus.

13. The system of claim 12, wherein the smallest value corresponds to a narrowband spectral modulation detection threshold that corresponds to the particular narrowband frequency range and that is included in the narrowband spectral modulation detection thresholds.

14. The system of claim 12, wherein the spectrally modulated electrical stimulus has a modulation frequency substantially equal to 0.5 cycles per octave.

15. The system of claim 12, wherein the spectrally modulated electrical stimulus has a modulation frequency substantially equal to 1.0 cycles per octave.

16. The system of claim 12, wherein the fitting station is configured to adjust the stimulation current by adjusting one or more stimulation parameters that control the stimulation current.

17. The system of claim 12, wherein the fitting station is further configured to reallocate the stimulation current between one or more narrowband frequency ranges in accordance with the narrowband spectral modulation detection thresholds.

18. The system of claim 12, wherein the spectrally modulated electrical stimulus has a ripple pattern.

19. The system of claim 12, further comprising:
an electrode array coupled to the implantable cochlear stimulator and having a plurality of electrodes disposed thereon;
wherein the implantable cochlear stimulator is configured to apply the flat electrical stimulus and the spectrally modulated electrical stimulus to one or more locations along a cochlea of the patient via one or more of the electrodes.

* * * * *